US009012135B2

(12) United States Patent
Haj-Ahmad (10) Patent No.: US 9,012,135 B2
(45) Date of Patent: Apr. 21, 2015

(54) METHODS, REAGENTS AND KITS FOR PRESERVATION OF NUCLEIC ACIDS IN BIOLOGICAL SAMPLES

(75) Inventor: Yousef Haj-Ahmad, St. Catharines (CA)

(73) Assignee: Norgen Biotek Corporation, Thorold, Ontario (CA)

( * ) Notice: Subject to any disclaimer, the term of this patent is extended or adjusted under 35 U.S.C. 154(b) by 0 days.

(21) Appl. No.: 13/524,560

(22) Filed: Jun. 15, 2012

(65) Prior Publication Data

US 2013/0149691 A1  Jun. 13, 2013

Related U.S. Application Data

(60) Provisional application No. 61/498,042, filed on Jun. 17, 2011, provisional application No. 61/543,532, filed on Oct. 5, 2011, provisional application No. 61/566,060, filed on Dec. 2, 2011.

(51) Int. Cl.
| | |
|---|---|
| C09K 15/18 | (2006.01) |
| G01N 1/30 | (2006.01) |
| C07H 21/00 | (2006.01) |
| A61K 31/132 | (2006.01) |
| C07H 21/02 | (2006.01) |
| A01N 1/02 | (2006.01) |
| C12N 15/10 | (2006.01) |
| C12Q 1/68 | (2006.01) |

(52) U.S. Cl.
CPC ............... *C09K 15/18* (2013.01); *C07H 21/00* (2013.01); *G01N 1/30* (2013.01); *A61K 31/132* (2013.01); *C07H 21/02* (2013.01); *A01N 1/0226* (2013.01); *C12N 15/1003* (2013.01); *C12Q 1/6806* (2013.01)

(58) Field of Classification Search
CPC ....... C12Q 1/6806; C12N 15/10; C07H 21/01; C07H 21/04
See application file for complete search history.

(56) References Cited

U.S. PATENT DOCUMENTS

| | | | | |
|---|---|---|---|---|
| 4,268,406 | A | * | 5/1981 | O'Brien et al. ............... 510/237 |
| 5,455,344 | A | * | 10/1995 | Harper et al. ............... 536/123.1 |
| 6,821,789 | B2 | | 11/2004 | Augello et al. |
| 7,282,371 | B2 | | 10/2007 | Helftenbein |
| 7,686,035 | B2 | | 3/2010 | Goinski |
| 2004/0038269 | A1 | * | 2/2004 | Birnboim ........................ 435/6 |
| 2007/0021591 | A1 | * | 1/2007 | Movius et al. ................ 530/350 |
| 2007/0202511 | A1 | * | 8/2007 | Chen et al. ......................... 435/6 |
| 2008/0146790 | A1 | | 6/2008 | Grolz |
| 2008/0187924 | A1 | * | 8/2008 | Korfhage et al. ................ 435/6 |
| 2009/0130714 | A1 | * | 5/2009 | Majumder et al. ........... 435/69.1 |
| 2013/0273607 | A1 | * | 10/2013 | O'Connor .................... 435/69.6 |

OTHER PUBLICATIONS

Subhasis Banerjee, Alan Smallwood, Anne E. Chambers, and Kypros Nicolaides, Quantitative recovery of immunoreactive proteins from clinical samples following RNA and DNA isolation, 2003, BioTechniques 35:450-456.*

(Continued)

*Primary Examiner* — Blaine Lankford
*Assistant Examiner* — Trent Clarke
(74) *Attorney, Agent, or Firm* — Harris, Shelton, Hanover & Walsh; Susan B Fentress

(57) ABSTRACT

Provided is a nucleic acid preservative comprising at least one reducing agent, at least one chaotropic substance, at least one polyamine substance and at least one chelating agent and uses thereof, and a method for the preservation of nucleic acids in a biological sample. Further provided are kits for use in the preservation of nucleic acids in a biological sample, and more particularly, a blood sample.

4 Claims, 9 Drawing Sheets

Day 0

Day 6

(56) References Cited

OTHER PUBLICATIONS pdf document 'Biuret Nov. 25, 2009' from website DTN/The Progressive Farmer at http://www.dtnprogressivefarmer.com/dtnag/view/ag/printablePage.do?ID=BLOG__PRINTABLE__PAGE&bypassCache=true&pageLayout=v4&blogHandle=production&blogEntryId=8a82c0bc2504791101252c20bb9701ee&articleTitle=What's+Biruet&editionName=DTNAgFreeSiteOnline, accessed Dec. 16, 2013.*

PAXgene Blood RNA Kit IVD, Sample & Assay Technologies;http://www.glagen.com/products/catalog/sample-technologies/ma-sample-technologies/total-ma/paxgene-blood-rna-kit-ivd.

PAXgene Blood DNA Kit; Sample & Assay Technologies; http://www.glagen.com/products/catalog/sample-technologies/dna-sample-technologies/genomic-dna/paxgene-blood-dna-kit.

* cited by examiner

METHODS, REAGENTS AND KITS FOR PRESERVATION OF NUCLEIC ACIDS IN BIOLOGICAL SAMPLES

FIELD OF INVENTION

The present invention relates to methods, reagents and kits useful for preservation of nucleic acids in biological samples, and in particular, blood samples.

BACKGROUND

Samples of blood are often collected for use in various applications such as diagnostics. Traditionally, the blood was collected in order to look at cellular morphology and to count cells. Conventional blood collection involves collecting the blood into tubes which contain various additives such as EDTA, heparin or citrate. These additives function as anticoagulants which allow for the blood samples to be stored for longer periods of time prior to analysis than if collected without the use of any additive. Currently, diagnostics is shifting towards a focus on molecular diagnostics, in which nucleic acids are isolated and studied. The analysis may include the use of various different methods including polymerase chain reaction (PCR), reverse transcription PCR (RT PCR), real time PCR, RNA and DNA chips, gene expression arrays, microarrays, and restriction fragment length polymorphism (RFLP) among others.

Blood is still a key biological sample which is being used for diagnostics, however, the traditional additives used for the preservation of blood offer a number of disadvantages when nucleic acids are to be isolated and analyzed. Nucleic acids in blood, and particularly RNA, are very unstable. The key to the successful analysis of nucleic acids isolated from blood is that the nucleic acid is of a high quality and that it remains intact from the time of sample collection until the nucleic acids can be isolated and analyzed in the lab. Once a blood sample has been obtained from an individual, a major problem is the stability of the nucleic acids within the sample. Nucleic acids in a biological sample quickly degrade at ambient temperature. Cells contain nucleases which quickly degrade and destroy nucleic acids as soon as they come into contact with DNA or RNA substrates. These nucleases are controlled due to their location in various compartments within the cells including lysosomes. However, when blood samples are drawn, the cells present in the blood will start to die, and these nucleases will be released from the lysosomes and will quickly begin to degrade the nucleic acids within the blood sample. Thus, this is a major problem with using blood samples as a source of nucleic acids for analysis. The stability of the nucleic acids within the blood sample must be maintained as this determines whether the nucleic acids can be successfully analyzed, be it for research or diagnostic purposes. Traditional blood preservatives, such as EDTA and heparin, do not allow for the preservation of the nucleic acids present within the blood sample and thus the DNA, and more specifically RNA, will quickly degrade in the presence of these additives.

In recent years, the study of gene expression has also been increasing, with gene activity and nucleic acids obtained from biological samples being used to diagnose infections or diseases including cancer, and to monitor the effects of administered drugs, among other applications. Therefore, in addition to the isolation of high quality nucleic acids from blood, it is also of interest to inhibit or block gene induction in an isolated blood sample such that the "snapshot" of the gene expression and levels at the moment the blood sample is drawn is maintained. When a sample of blood is drawn induction of gene transcription may occur, with over-production or under-production of some mRNA species. This will result in changes in the transcript pattern of the sample and subsequent analysis of gene expression will therefore be altered. Therefore inhibiting or blocking gene induction immediately upon the collection of blood samples is highly important for many downstream applications of the blood sample. Again, traditional blood preservation additives such as EDTA and heparin will not function to inhibit gene induction.

Another important aspect of preserving blood samples for use in molecular applications is that the sample should be preserved at room temperature for extended periods of time in order to allow for ease of shipping of the sample. Samples are often collected in one location, and then shipped to another location for analysis. If a blood sample can be stored and shipped at room temperature while preserving the integrity of the nucleic acids this would be of a great benefit in terms of ease of shipping and shipping costs. As well, this would be a key for blood samples which are collected in remote locations or in resource-limited settings where refrigerators and freezers for storage of the blood samples may not be available.

Another major concern with the collection and transport of blood samples for nucleic acid analysis is that these samples are often infectious, as the sample may contain live virus or bacteria. The presence of live infectious pathogens in these biological samples poses a health and safety risk to the individuals involved in the collection, transfer and testing of the samples if the samples are kept viable and/or biologically intact. Due to the potential dangers of shipping biologically intact samples the expense and effort required in shipping these samples is increased.

SUMMARY OF INVENTION

In a first aspect, provided is a nucleic acid preservative comprising at least one reducing agent, at least one chaotropic substance, at least one polyamine substance and at least one chelating agent.

In an embodiment, the reducing agent is glutathione.

In a further embodiment, the glutathione is present in an amount from about 10 mM to about 200 mM.

In a further embodiment, the chaotropic substance is a lithium salt.

In a further embodiment, the lithium salt is present in an amount from about 1 M to about 4 M.

In a further embodiment, the lithium salt is LiCl.

In a further embodiment, the chaotropic substance is a guanidium salt.

In a further embodiment, the guanidium salt is present in an amount from about 0.1 M to about 0.9 M.

In a further embodiment, the guanidium salt is guanidine hydrochloride.

In a further embodiment, the chaotropic substance is urea.

In a further embodiment, the urea is present in an amount from about 2 M to about 12 M.

In a further embodiment, the polyamine substance is spermidine.

In a further embodiment, the spermidine is present in an amount from about 10 μM to about 300 μM.

In a further embodiment, the polyamine substance is biuret.

In a further embodiment, the biuret is present in an amount of about 10 mM to about 100 mM.

In a further embodiment, the chelating agent is EDTA.

In a further embodiment, the EDTA is present in an amount of from about 1 mM to about 200 mM.

In a further embodiment, the reducing agent is glutathione, wherein the glutathione is present in an amount from about 10 mM to about 200 mM; a first chaotropic substance is LiCl, wherein the LiCl is present in an amount of from about 1 M to about 4 M; a second chaotropic substance is guanidine hydrochloride, wherein the guanidine hydrochloride is present in an amount from about 0.1M to about 0.9 M; a third chaotropic substance is urea, wherein the urea is present in an amount from about 2 M to about 12 M; a first polyamine substance is spermidine, wherein the spermidine is present in an amount from about 10 µM to about 300 µM, a second polyamine substance is biuret, wherein the biuret is present in an amount of from about 10 mM to about 100 mM; and the chelating agent is EDTA, wherein the EDTA is present in an amount of from about 1 mM to about 200 mM.

In a further aspect, provided is a method for preserving nucleic acids in a biological sample, comprising the steps of: providing a nucleic acid preservative comprising at least one reducing agent, at least one chaotropic substance, at least one polyamine substance and at least one chelating agent; and combining the biological sample with the nucleic acid preservative.

In an embodiment, the reducing agent is glutathione and wherein the glutathione is present in an amount from about 10 mM to about 200 mM.

In a further embodiment, the chaotropic substance is a lithium salt and wherein the lithium salt is present in an amount from about 1M to about 4 M.

In a further embodiment, the lithium salt is LiCl.

In a further embodiment, the chaotropic substance is a guanidium salt, and wherein the guanidium salt is present in an amount from about 0.1M to about 0.9 M.

In a further embodiment, the guanidium salt is guanidine hydrochloride.

In a further embodiment, the chaotropic substance is urea and wherein the urea is present in an amount from about 2M to about 12 M.

In a further embodiment, the polyamine substance is spermidine and wherein the spermidine is present in an amount from about 10 µM to about 300 µM.

In a further embodiment, the polyamine substance is biuret and wherein the biuret is present in an amount of about 10 mM to about 100 mM.

In a further embodiment, the chelating agent is EDTA and wherein the EDTA is present in an amount of from about 1 mM to about 200 mM.

In a further embodiment, the reducing agent is glutathione, wherein the glutathione is present in an amount from about 10 mM to about 200 mM; a first chaotropic substance is LiCl, wherein the LiCl is present in an amount of from about 1M to about 4 M; a second chaotropic substance is guanidine hydrochloride, wherein the guanidine hydrochloride is present in an amount from about 0.1M to about 0.9 M; a third chaotropic substance is urea, wherein the urea is present in an amount from about 2M to about 12 M; a first polyamine substance is spermidine, wherein the spermidine is present in an amount from about 10 µM to about 300 µM, a second polyamine substance is biuret, wherein the biuret is present in an amount of from about 10 mM to about 100 mM; and the chelating agent is EDTA, wherein the EDTA is present in an amount of from about 1 mM to about 200 mM.

In a further embodiment, the biological sample is a blood sample.

In a further embodiment, the nucleic acid is RNA, DNA or combination thereof.

In a further embodiment, the nucleic acid is cell-free plasma RNA.

In a further aspect, provided is the use of the nucleic acid preservative as disclosed herein for the preservation of nucleic acid in a biological sample.

In an embodiment, the biological sample is a blood sample.

In a further embodiment, the biological sample is a whole blood sample.

In a further embodiment, the nucleic acid is RNA, DNA or combination thereof.

In a further embodiment, the nucleic acid is cell-free plasma RNA.

In a further aspect, provided is the use of the nucleic acid preservative as disclosed herein for inhibition of gene induction in a biological sample.

In an embodiment, the biological sample is a blood sample.

In a further embodiment, the biological sample is a whole blood sample.

In another aspect, provided is a kit for the preservation of nucleic acids in a biological sample, said kit comprising: the nucleic acid preservative as disclosed herein; and instructions for the use of said nucleic acid preservative.

In an embodiment, the nucleic acid preservative is an aqueous solution.

In a further embodiment, the nucleic acid preservative is lyophilized.

In a further aspect, provided is a kit for the preservation of nucleic acids in a biological sample, wherein the biological sample is a blood sample, said kit comprising: an evacuated tube containing a predetermined amount of an anticoagulant for blood collection; a syringe containing a predetermined amount of the nucleic acid preservative as disclosed herein; and instructions for the use of the nucleic acid preservative.

In an embodiment, the kit further comprises a needle attachable to the syringe.

In a further aspect, provided is a kit for the preservation of nucleic acids in a biological sample, wherein the biological sample is a blood sample, said kit comprising: an evacuated tube containing a predetermined amount of an anticoagulant for blood collection; a sealed, squeezable ampule, containing a predetermined amount of the nucleic acid preservative as disclosed herein; wherein said ampule comprises a removable closure and wherein said ampule is configured to receive a dispensing means upon removal of the closure by a user, and instructions for the use of said nucleic acid preservative.

In an embodiment, the kit further comprises a dispensing means attachable to said ampule following removal of said closure by a user, wherein the dispensing means is a needle or a dispensing pin.

In a further embodiment, the sealed, squeezable ampule contains about 6 mL of the nucleic acid preservative.

BRIEF DESCRIPTION OF THE DRAWINGS

Preferred embodiments of the invention will now be described, by way of example, with reference to the accompanying drawings, in which.

DESCRIPTION

Provided is a nucleic acid preservative that can be used to preserve and stabilize nucleic acids found in biological samples, and in particular, blood samples. As used herein, the term "nucleic acid" includes both ribonucleic acid (RNA) and deoxyribonucleic acid (DNA) and further includes RNA and/or DNA which is linear or branched, single or double stranded or fragments thereof. The nucleic acid may be of any biological origin, and in particular, may be nucleic acid found in blood, including cell-free plasma RNA such as microRNA.

When biological samples are treated with the nucleic acid preservative disclosed herein, the nucleic acids found in the biological samples are preserved and stabilized whereby the nucleic acids are protected from degradation and can be later isolated from the biological sample and analyzed using conventional molecular biology techniques. Nucleic acids preserved using the nucleic acid preservative of the present application can be isolated from treated biological samples following extended periods of storage over a range of temperatures and can be used in diagnostic applications.

The nucleic acid preservative disclosed herein is also useful for inhibiting or blocking gene induction in a biological sample. As discussed above, it useful to take a "snapshot" of the levels of gene expression at the time a biological sample is taken.

The nucleic acid preservative disclosed herein is further useful for the lysis of viruses, bacteria and fungi that may be present in the biological sample thereby reducing the health and safety risks associated with handling and transporting the treated biological sample.

In one aspect, provided is a nucleic acid preservative comprising at least one reducing agent, at least one chaotropic substance, at least one polyamine substance and at least one chelating agent.

The reducing agent can preferably be glutathione (GSH). The nucleic acid preservative may comprise from about 10 mM to about 200 mM of glutathione, preferably from about 10 mM to about 100 mM of glutathione, more preferably from about 10 mM to about 50 mM of glutathione, even more preferably from about 10 mM to about 25 mM of glutathione, and still more preferably about 15 mM of glutathione.

The chaotropic substance can preferably be a lithium salt and more preferably, LiCl. The nucleic acid preservative may comprise from about 1 M to about 4 M of the lithium salt, preferably from about 2 M to 3 M of the lithium salt, and more preferably, about 2 M of the lithium salt.

The chaotropic substance can preferably be a guanidium salt, and more preferably, guanidine hydrochloride. The nucleic acid preservative may comprise from about 0.1 M to 0.9 M of the guanidine hydrochloride, preferably from about 0.5 M to about 0.9 M of the guanidine hydrochloride, more preferably about 0.7 M of the guanidine hydrochloride.

The chaotropic substance can preferably be urea. The nucleic acid preservative may comprise from about 2 M to about 12 M of urea, preferably about 5 M to about 10 M of urea, more preferably about 6 M to about 9 M of urea and even more preferably about 8 M of urea.

In a preferred embodiment, the nucleic acid preservative may comprise one or more of a lithium salt, a guanidine salt or urea. In a still further preferred embodiment, the nucleic acid preservative may comprise one or more of LiCl, guanidine hydrochloride or urea.

The polyamine substance can preferably be spermidine. The nucleic acid preservative may comprise from about 10 μM to about 300 μM of spermidine, preferably from about 50 μM to about 300 μM of spermidine, more preferably from about 100 μM to about 200 μM of spermidine, even more preferably about 100 μM of spermidine.

The polyamine substance can preferably be biuret. The nucleic acid preservative may comprise from about 10 mM to about 100 mM of biuret, preferably from about 10 mM to about 50 mM of biuret, more preferably from about 10 mM to about 30 mM of biuret, and even more preferably about 30 mM of biuret.

In a preferred embodiment, the nucleic acid preservative may comprise one or more of spermidine or biuret.

The chelating agent can preferably be EDTA. The nucleic acid preservative may comprise from about 1 mM to about 200 mM of EDTA, preferably from about 1 mM to about 100 mM of EDTA, more preferably from about 1 mM to about 10 mM of EDTA, and even more preferably about 5 mM of EDTA.

In a further preferred embodiment, the nucleic acid preservative comprises glutathione as a reducing agent, wherein the glutathione is present in an amount from about 10 mM to about 200 mM; LiCL as a first chaotropic substance, wherein the LiCl is present in an amount of from about 1 M to about 4 M; guanidine hydrochloride as a second chaotropic substance is, wherein the guanidine hydrochloride is present in an amount from about 0.1 M to about 0.9 M; urea as a third chaotropic substance, wherein the urea is present in an amount from about 2 M to about 12 M; spermidine as a first polyamine substance, wherein the spermidine is present in an amount from about 10 µM to about 300 µM; biuret as a second polyamine substance, wherein the biuret is present in an amount of from about 10 mM to about 100 mM; EDTA as a chelating agent is EDTA, wherein the EDTA is present in an amount of from about 1 mM to about 200 mM.

The nucleic acid preservative disclosed herein can be used to preserve and stabilize nucleic acids in a biological sample. The nucleic acid preservative can also be used to inhibit or block gene induction in a biological sample. The nucleic acid preservative can further be used for cell lysis in the biological sample. In preferred embodiments, the biological sample is a blood sample, and more preferably a whole blood sample.

In a further aspect, provided is a method for preserving nucleic acids in a biological sample, comprising the steps of: providing a nucleic acid preservative comprising at least one reducing agent, at least one chaotropic substance, at least one polyamine substance and at least one chelating agent, and combining the biological sample with the nucleic acid preservative.

The biological sample, and more preferably a blood sample, can be collected directly or indirectly into any suitable container and a suitable amount of the nucleic acid preservative added to the blood sample. In one embodiment, the biological sample is preferably a blood sample, and more preferably a human blood sample. It is contemplated that the amount of the nucleic acid preservative to be added to a biological sample for preservation of the nucleic acids contained in the biological sample, inhibition of gene induction and cell lysis can be determined by the person skilled in the art by routine experimentation.

In a preferred embodiment, a predetermined amount of the nucleic acid preservative is provided in a container, such as an evacuated tube, into which the blood sample can be directly collected such that the blood sample immediately comes into contact with the nucleic acid preservative. The amount of blood to be collected will be in a predetermined ratio with the amount of nucleic acid preservative present contained in the container such that the nucleic acids contained in the sample are preserved, gene induction is inhibited and all cells present are lysed.

In another preferred embodiment, the nucleic acid preservative is provided as a liquid and more preferably as an aqueous solution. The aqueous solution may be provided contained in a syringe, an ampule, a dissolvable capsule, a permeable sack or other vehicle. The nucleic acid preservative can also be provided in solid form such as granules or tablets. The nucleic acid preservative can also be prepared as an aqueous solution which is then lyophilized. The lyophilized nucleic acid preservative can be provided in dry form for use or can be reconstituted with a suitable carrier prior to use.

In another preferred embodiment, a predetermined amount of the nucleic acid preservative is provided as a liquid in a syringe attached to a needle (or in a syringe and a separate needle to be attached by the user), such that the nucleic acid preservative can be added directly to a blood sample which has been collected into an evacuated tube by piercing the self-sealing closure of the evacuated tube with the needle and depressing the plunger of the syringe to expel the nucleic acid preservative from the syringe into the evacuated tube containing the blood sample and optionally, any anticoagulant known in the art. The amount of blood to be collected in the evacuated tube will be in a predetermined ratio with the amount of nucleic acid preservative contained in the syringe such that the nucleic acids contained in the sample are preserved, gene induction is inhibited and all cells present are lysed. The ratio of nucleic acid preservative to blood may be between about 3:1 to about 1:1 v/v and, more preferably about 2:1 v/v.

In another preferred embodiment, a predetermined amount of the nucleic acid preservative is provided as a liquid in a sealed, squeezable, plastic ampule having a removable closure. Upon removal of the closure, a dispensing means, such as a conventional needle or dispensing pin, can be attached to the ampule to facilitate the addition of the nucleic acid preservation to a biological sample to be treated. In use, the nucleic acid preservative can be added directly to a biological sample, and more preferably, a blood sample which has been collected into an evacuated tube. The needle or dispensing pin is used to pierce the self-sealing closure of the evacuated tube and the ampule body is squeezed to expel the nucleic acid preservative into the evacuated tube containing the blood sample and optionally, any anticoagulant known in the art. The amount of blood to be collected in the evacuated tube will be in a predetermined ratio with the amount of nucleic acid preservative contained in the ampule such that the nucleic acids contained in the sample are preserved, gene induction is inhibited and all cells present are lysed. The ratio of nucleic acid preservative to blood may be between about 3:1 to about 1:1 v/v and, more preferably about 2:1 v/v.

FIGS. 1A-C and 2A-D illustrate a first embodiment of an ampule for containing the nucleic acid preservative. The ampule 10 comprises a generally tubular body 12 defining a cavity for containing the predetermined amount of nucleic acid preservative. In a preferred embodiment, the body 12 is sized to contain about 6 ml of the nucleic acid preservative. An upper portion 14 of the body 12 is joined to a neck 16 which defines an opening 18 for receiving the nucleic acid preservative. In a preferred embodiment, the body 12 is sized to contain about 6 ml of the nucleic acid preservative. The body 12 may be about 48 mm in length from the base of the ampule to the bottom of the neck portion 16 and have an outer diameter of about 15 mm. The neck portion 16 may be about 10 mm in length and have an outer diameter of about 4.5 mm. The dimensions of the ampule can adapted to accommodate smaller and larger volumes of the nucleic acid preservative.

Figure 1A:
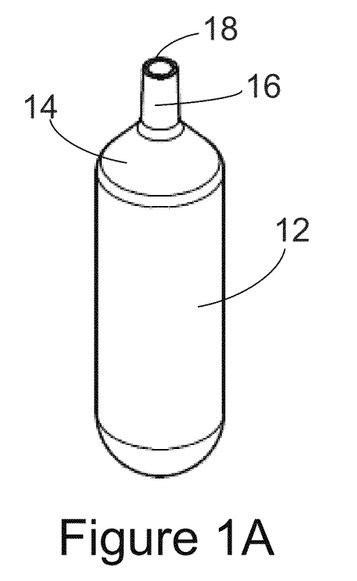
FIG. 1A is a perspective view of a first embodiment of an ampule without a closure.
Figure 1B:
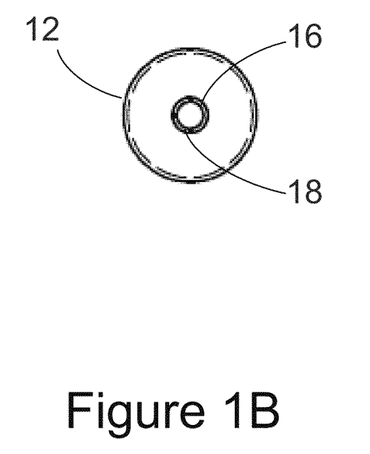
FIG. 1B is a top plan view of the ampule of FIG. 1A.
Figure 1C:
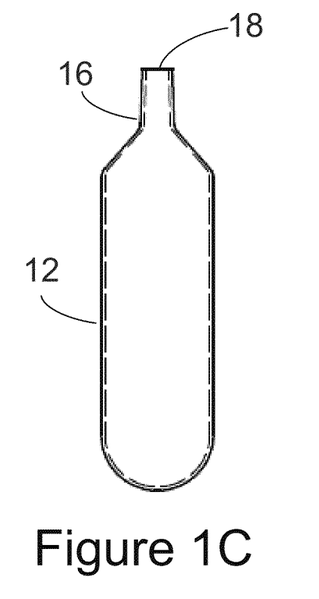
FIG. 1C is a cross-sectional side view of the ampule of FIG. 1A.
Figure 2A:
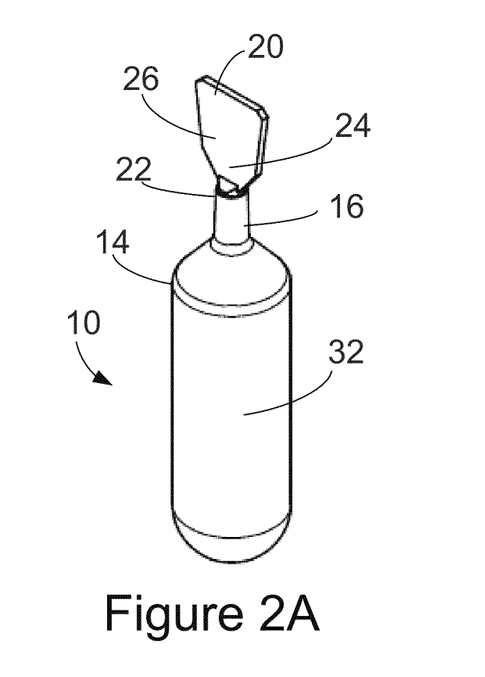
FIG. 2A is a perspective view of the ampule of FIG. 1A with a closure.
Figure 2B:
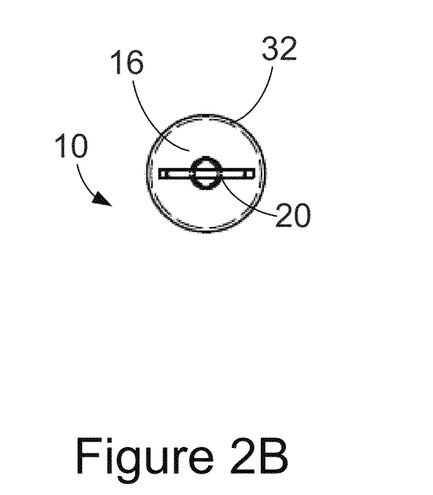
FIG. 2B is a top plan view of the ampule of FIG. 2A.
Figure 2C:
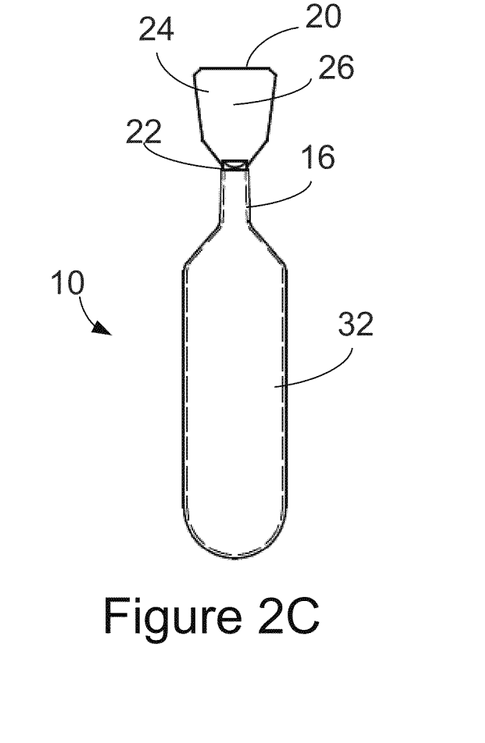
FIG. 2C is a cross-sectional front view of the ampule of FIG. 2A.
Figure 2D:
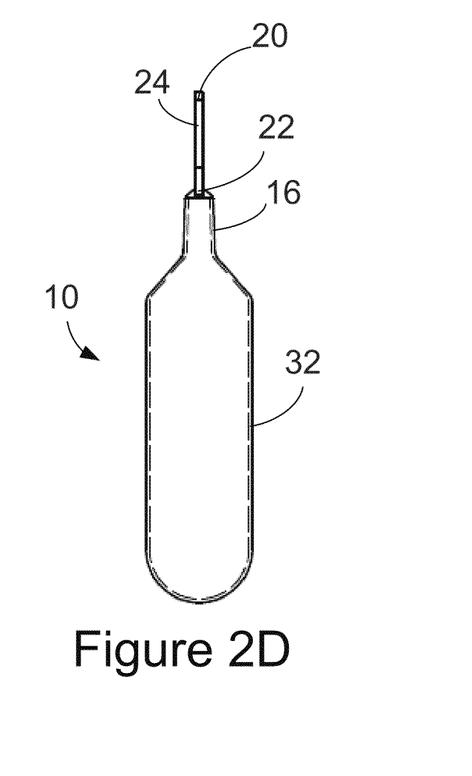
FIG. 2D is a cross-section side view of the ampule of FIG. 2A.

The neck 16 can be sized and configured to accept a conventional needle (for example, but not limited, to luer slip-on needles provided by Becton Dickinson, Franklin Lakes, N.J., USA). Alternatively, the neck 16 can be sized and configured to accept a conventional dispensing pin (for example, but not limited to Mini-spike dispensing pins provided by B. Braun Medical Inc., Bethlehem, Pa., USA).

The body 12 and neck 16 can be formed as a unitary structure of moulded, flexible plastic, such as, but not limited to polypropylene or polyethylene.

In use, the body 12 is filled with the predetermined amount of nucleic acid preservative using conventional methods, such as pipetting, and the opening 18 sealed with closure 20 as shown in FIGS. 2A-D. Closure 20 comprises a lower portion 22 and an upper portion 24 and a predetermined line of weakness 26 (not shown) between the lower and upper portions 22 and 24. The lower portion 22 is generally tubular and can be sized and configured to be received in the opening 18 of the neck 16 to form a seal. Alternatively, the lower portion 22 can be sized and configured to be received over the opening 18 of the neck 16 to form a seal. The interface between the neck 16 and the lower portion 22 of the closure 20 can be made liquid impermeable by heat sealing to provide a sealed ampule. The upper portion 24 of the closure 20 is generally planar providing a grasping surface 26 for a user.

In use, to remove the closure 20 from the sealed ampule 10, a user can grasp and twist the upper portion 24 of the closure 20 thereby separating the lower and upper portions 22 and 24 along the line of weakness 26. The user can then pull off the upper portion 24 of the closure 20 to expose the opening 18 of the ampule 10.

Figure 6:
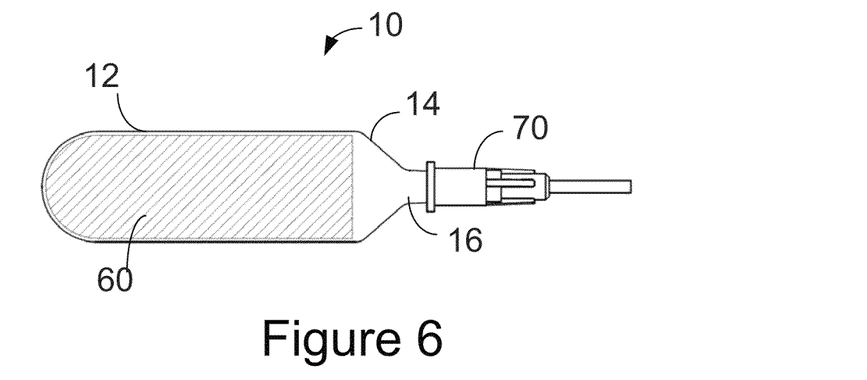
FIG. 6 is a side view of the ampule of FIG. 5 with the closure replaced with a syringe.
Figure 7:
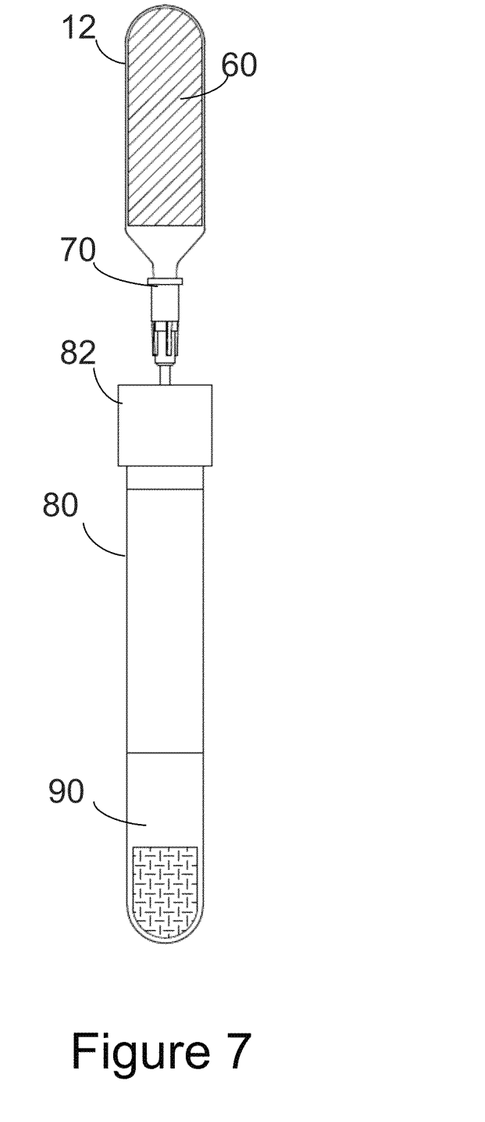
FIG. 7 is a side view of the ampule of FIG. 6 with the syringe inserted into an evacuated container containing a blood sample.
Figure 8:
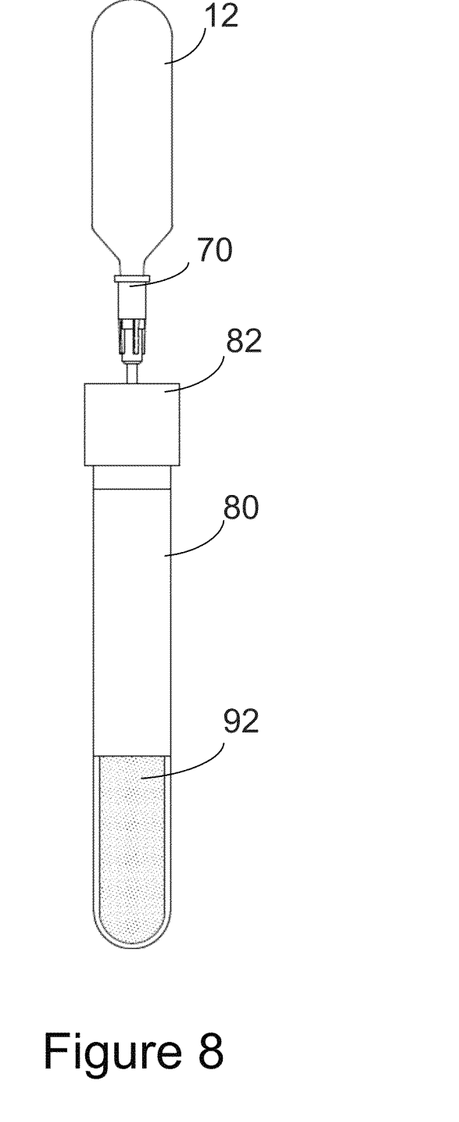
FIG. 8 is a side view of the ampule and evacuated container of FIG. 7, wherein the nucleic acid preservative has been transferred from the ampule to the evacuated container.

Following removal of the closure 20, a conventional needle or dispensing pin can be attached onto the neck 16 by slipping the needle or dispensing pin onto to the neck of the ampule. FIG. 6 illustrates the attachment of a needle 70 onto the neck 16 of the ampule 10. As seen in FIGS. 7 and 8, the needle 70 (or alternatively, a dispensing pin) can be inserted into a self-sealing closure 82 of a conventional evacuated container 80 containing a blood sample 90 in order to transfer the nucleic acid preservative 60 from the ampule 10 into the evacuated container 90. The nucleic acid preservative 60 can be expelled from the body 12 of the ampule 10 through the needle 70 (or alternatively, a dispensing pin) and into the evacuated container 90 by squeezing the body 12 of the ampule 10 whereby the nucleic acid preservative 60 is combined with the blood sample 90 to provide a preserved sample 92.

FIGS. 3A-C and 4A-D illustrate a second embodiment of an ampule for containing the nucleic acid preservative. The ampule 30 comprises a generally tubular body 32 defining a cavity for containing the predetermined amount of nucleic acid preservative. An upper portion 34 of the body 32 is joined to a neck 36 which defines an opening 38 for receiving the nucleic acid preservative. An upper portion 34 of the body 32 is further joined a threaded collar 40 which encircles at least a portion of the neck 36. In a preferred embodiment, the body 32 is sized to contain about 6 ml of the nucleic acid preservative. The body 32 may be about 48 mm in length from the base of the ampule to the base of the neck portion 36 and have an outer diameter of about 15 mm. The neck portion 36 may be about 10 mm in length and have an outer diameter of about 4.5 mm. The threaded collar 40 may be about 8.6 mm in length have an outer diameter of about 9 mm. The dimensions of the ampule can adapted to accommodate smaller and larger volumes of the nucleic acid preservative.

Figure 3A:
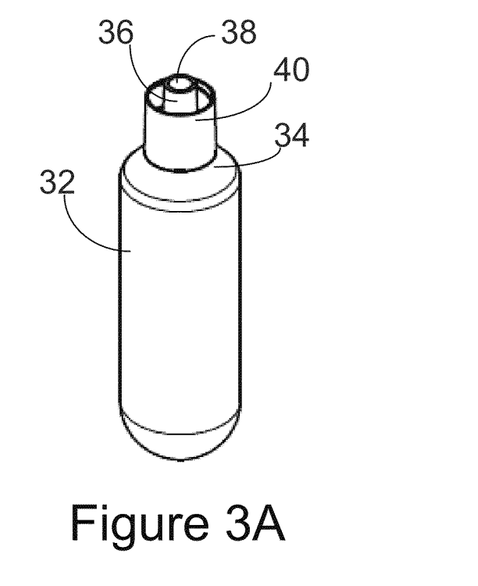
FIG. 3A is a perspective view of a second embodiment of an ampule without a closure.
Figure 3B:
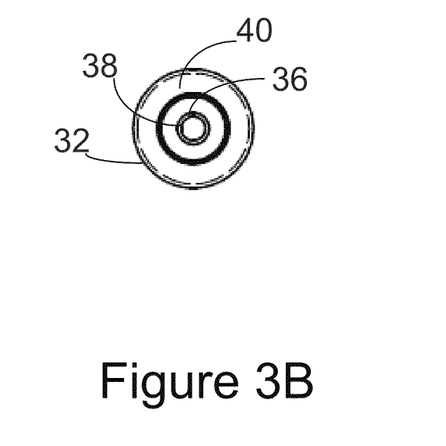
FIG. 3B is a top plan view of the ampule of FIG. 3A.
Figure 3C:
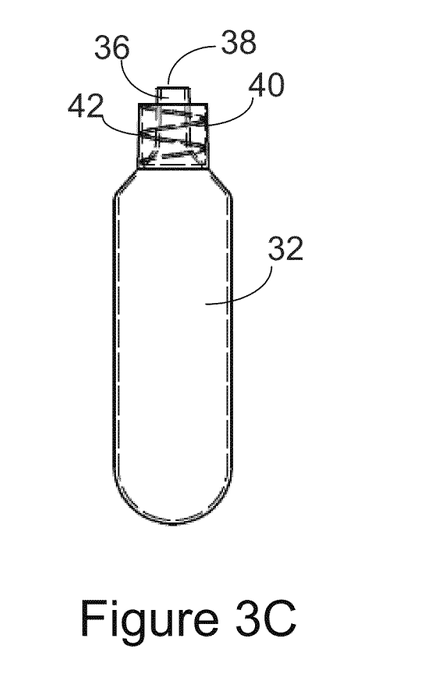
FIG. 3C is a cross-sectional side view of the ampule of FIG. 3A.
Figure 4A:
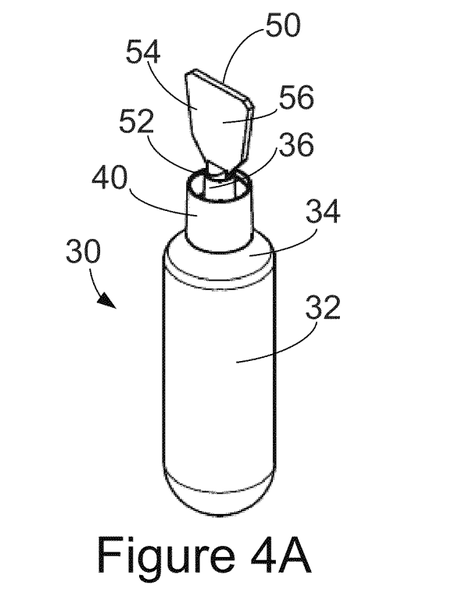
FIG. 4A is a perspective view of the ampule of FIG. 3A with a closure.
Figure 4B:
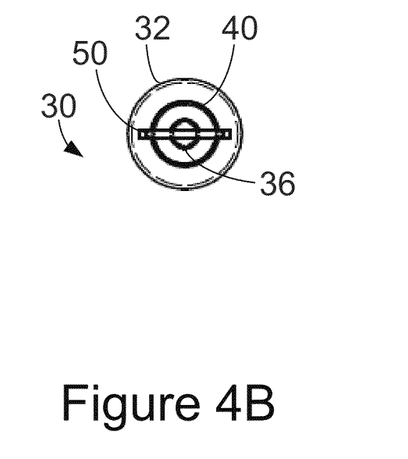
FIG. 4B is a top plan view of the ampule of FIG. 4A.
Figure 4C:
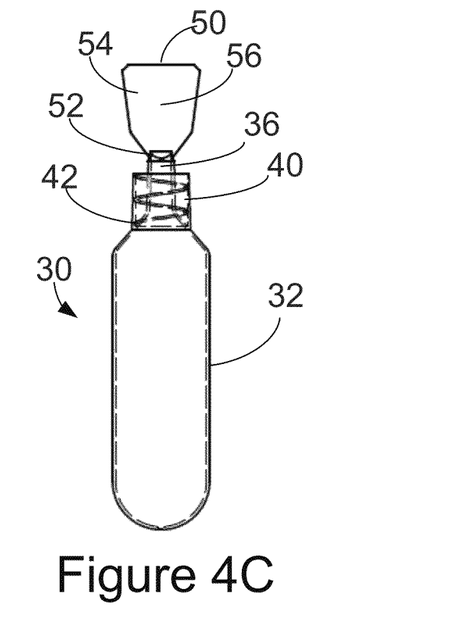
FIG. 4C is a cross-sectional front view of the ampule of FIG. 4A.
Figure 4D:
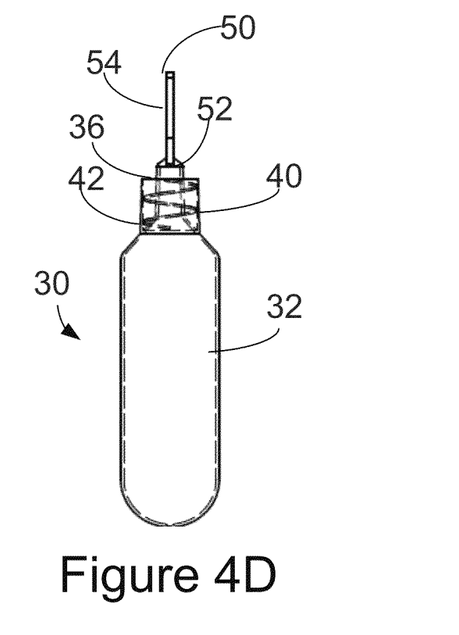
FIG. 4D is a cross-section side view of the ampule of FIG. 4A.
Figure 5:
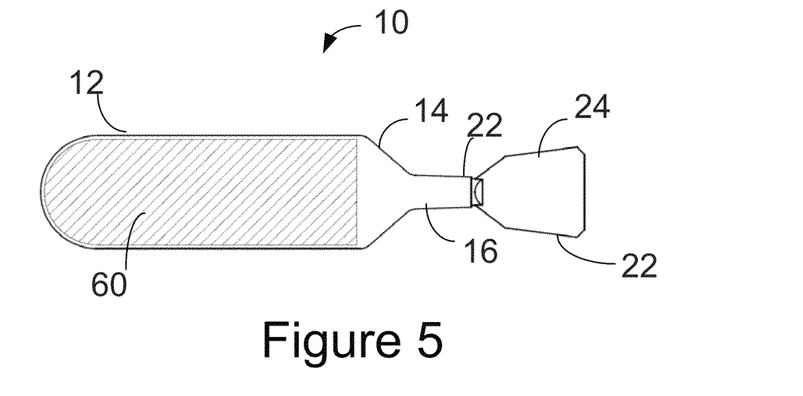
FIG. 5 is a side view of an embodiment of an ampule containing a nucleic acid preservative.

The neck 36 and threaded collar 40 can be sized and configured to accept a conventional luer lock needle (for example, but not limited to, luer lock needles provided by Becton Dickinson, Franklin Lakes, N.J., USA). Alternatively, neck 36 and threaded collar 40 can be sized and configured to accept a conventional dispensing pin having a luer connection (for example, but not limited, to Mini-Spike® dispensing pins having a luer connection provided by B. Braun Medical Inc., Bethlehem, Pa., USA).

The body 32, neck 36 and threaded collar 40 can be formed as a unitary structure of moulded, flexible plastic, such as, but not limited to polypropylene or polyethylene.

In use, the body 32 is filled with the predetermined amount of nucleic acid preservative using conventional methods, such as pipetting, and the opening 38 sealed with closure 50 as shown in FIGS. 4A-D. Closure 50 comprises a lower portion 52 and an upper portion 54 and a predetermined line of weakness 56 (not shown) between the lower and upper portions 52 and 54. The lower portion 52 is generally tubular and can be sized and configured to be received in the opening 38 of the neck 36 to form a seal. Alternatively, the lower portion 52 can be sized and configured to be received over the opening 38 of the neck 36 to form a seal. The interface between the neck 36 and the lower portion 52 can be made liquid impermeable by heat sealing to provide a sealed ampule. The upper portion 54 of the closure 50 is generally planar providing a grasping surface 56 for a user.

In use, to remove the closure 50 from the sealed ampule 30, a user can grasp and twist the upper portion 54 of the closure 50 thereby separating the closure 50 along the line of weakness 56. The user can pull off the upper portion 54 of the closure 50 to expose the opening 38 of the ampule 30.

Following removal of the closure 50, a conventional luer lock needle or a dispensing pin having a luer connection can be attached onto the neck 36 by screwing the needle or dispensing pin onto to the neck 36 of the ampule 30. The needle (or alternatively, the dispensing pin) can then be inserted into a self-sealing closure of an evacuated container containing a biological sample, and more preferably, a blood sample. The nucleic acid preservative can be expelled from the body 32 of the ampule 30 through the needle or the dispensing pin into the evacuated container by squeezing the body 32 of the ampule 30 whereby the nucleic acid preservative is combined with the blood sample to provide a preserved sample.

The nucleic acid preservative disclosed herein is useful for the preservation of nucleic acids in biological samples for both short and longer term storage and under varying temperature conditions. The time period for nucleic acid preservation may be as short as the time necessary to transfer a sample from the point of collection to the point of analysis, or it may be for extended periods of time. The nucleic acid preservative can be used to preserve nucleic acids in a biological sample for a period of several minutes, hours, days, or greater. In one preferred embodiment of this invention, the nucleic acid preservative can be used to preserve RNA and DNA found in blood samples for extended periods. For example, blood RNA can be preserved at room temperature for over 16 days and blood DNA can be preserved at room temperature for over 20 days.

The temperature conditions under which the biological sample may be stored once the nucleic acid preservative has been added is not limited to room temperature. While the preferred embodiments of the invention refers to room temperature storage and shipping, which is generally from 15° C. to 30° C., in other embodiments the samples may be stored in cool environments. In other embodiments, the samples can be stored at 4° C., and in other embodiments the samples are stored at −20° C. for subsequent isolation and analysis of the intact, non-degraded nucleic acids from the stored sample.

After storage, the blood DNA and/or RNA can be isolated from the biological sample using methods known in the art, including spin column chromatography. Those skilled in the art will recognize that there are many different methods which can be used to isolate the DNA and/or RNA from the nucleic acid preservative for downstream analysis. Once isolated, the nucleic acids can then analyzed by any technique known in the art which can be used for analyzing nucleic acids, preferentially by gel electrophoresis or PCR amplification techniques.

In a further aspect, provided is a kit for preserving nucleic acids in a biological sample. The kit can be used for practicing the methods disclosed herein. The kit may comprise the nucleic acid preservative disclosed herein; and instructions for the use of said nucleic acid preservative. The nucleic acid preservative may be provided in liquid form as an aqueous solution. The aqueous solution may be provided contained in a dissolvable capsule, a permeable sack or other vehicle. The nucleic acid preservative may be provided in solid form as granules or tablets. The nucleic acid preservative may be provided in a lyophilized form which may be reconstituted into an aqueous solution prior to use. The nucleic acid preservative may be provided in a predetermined amount in a sample container for collecting the biological sample.

In a further aspect, provided is a kit for the preservation of nucleic acids in blood samples, said kit comprising: an evacuated tube containing an anticoagulant for blood collection, a syringe or an ampule containing a pre-aliquoted amount of nucleic acid preservative, and instructions for the use of said kit to preserve nucleic acids in blood samples. The syringe or ampule can be provided with a needle or a dispensing pin (or alternatively, a needle or a dispensing pin can be added by a user at the point of injection). In use, a predetermined amount of blood can be collected into the evacuated tube and briefly mixed with the anticoagulant, and then the pre-aliquoted nucleic acid preservative can then added to the blood sample by inserting the needle into the rubber stopper on the evacuated tube and either depressing the plunger of the syringe or squeezing the body of the ampule to transfer the nucleic acid preservative into the evacuated tube. The amount of blood to be collected and the amount of nucleic acid preservative present in the syringe or ampule are at an optimal ratio such that the nucleic acids contained in the sample are preserved, gene induction is inhibited and all cells present are lysed. The ratio of nucleic acid preservative to blood may be between about 3:1 to about 1:1 v/v and, more preferably about 2:1 v/v. In use, the kit allows for improved safety over conventional blood collection devices. An advantage of this kit over collecting blood directly into an evacuated tube containing a nucleic acid preservative is the increased safety in that there is no contact between the blood donor and the preservative itself which may pose health and safety risks.

While only specific embodiments of the invention have been described, it is apparent that variations can be made thereto without departing from the scope of the invention. The invention is further illustrated by the following examples, which are not to be construed in any way as imposing limitations upon the scope thereof. It is the intention in the appended claims to cover all variations that may fall within the true scope of the invention.

Example 1

Comparison of Blood RNA Stored and Preserved in Novel Nucleic Acid Preservative and with Conventional Heparin Additives Fifty mL blood samples were obtained from two individual donors by drawing 10 mL blood samples into BD Vacutainer™ Tubes supplemented with sodium heparin. Immediately, 3 mL aliquots of the blood were removed and mixed with 6 mL of the novel nucleic acid preservation solution (15 mM GSH, 2M LiCl, 0.7 M GnHCl, 8 M urea, 100 mM Spermidine, 30 mM Biuret and 5 mM EDTA) and stored at room temperature for 6 days. As a control, blood samples from the 2 donors were also incubated at room temperature in the sodium heparin tubes for 6 days. At time 0 and 6 days, RNA was isolated from the preserved blood using Norgen Biotek Blood RNA/DNA Preservation and Isolation Kit (Cat #48900, Norgen Biotek Corp., Thorold, Canada) and from the sodium heparin control blood using lithium chloride RNA precipitation from the 2 different donors. For the preserved blood, 1.5 mL RNA Extraction Buffer A and 1.5 mL RNA Extraction Buffer was added to the 9 mL preserved blood sample and vortexed for 30 seconds at high speed. Next, the tube was incubated at −20° C. for 10 minutes, followed by centrifugation at 6,000 RPM for 25 minutes. The supernatant was decanted and 570 μL, of Resuspension Buffer was added to the pellet and the tube was vortexed. Next, 330 μL of 95% ethanol was added to the tube and the tube again vortexed to mix. Next, 450 μL of the lysate was added to a silicon carbide-based spin column and centrifuged for 1 minute at 14,000 rpm. This binding step was repeated with the remaining 450 μL of lysate. The column was then washed 3 times with 600 μL of Wash Solution by spinning at 14,000 rpm for 1 minute. A dry spin was then performed by spinning at 14,000 rpm for 3 minutes. The RNA was eluted in 100 μL of Elution Buffer by spinning at 2,000 rpm for 2 minutes followed by 14,000 rpm for 2 minutes. To analyze the integrity of the RNA, 10 μL of each 100 μL elution was loaded onto a 1X MOPS 1.0%-Formaldehyde-agarose gel.

Figure 9:
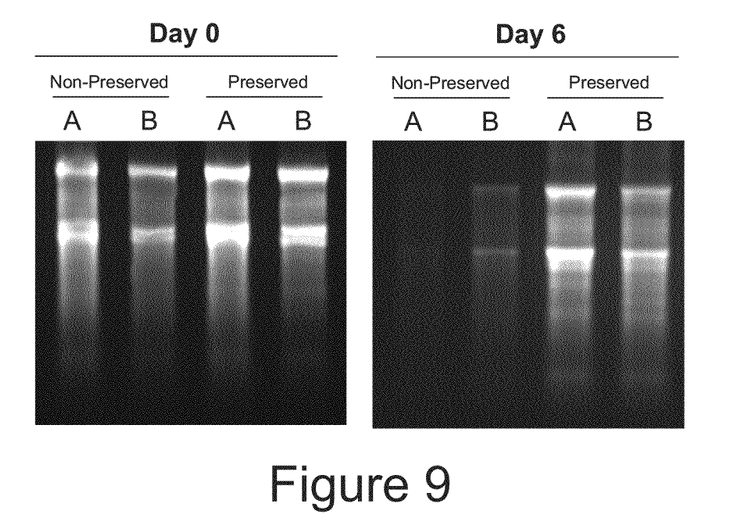
FIG. 9 shows formaldehyde-agarose gel images comparing the integrity of blood RNA from 2 donors (A and B) after 0 and 6 days storage at room temperature. The blood RNA was isolated from blood treated with a nucleic acid preservative as disclosed herein (Preserved) or from control blood stored in sodium heparin tubes (Non-preserved).

The gel images in FIG. 9 clearly indicate that blood RNA which been stored in the preservation solution for up to 6 days at room temperature had been preserved and stabilized (i.e. non-degraded), as both the 28S rRNA and 18S rRNA appear as a clear band that is still intact from both donors. In contrast, after 6 days storage at room temperature the RNA from the non-preserved blood had been degraded.

Example 2

Storage and Preservation of Blood RNA for 12 Days at Room Temperature

Fifty mL blood samples were obtained from individual donors by drawing 10 mL blood samples into BD Vacutainer™ Tubes supplemented with sodium heparin. Immediately 3 mL aliquots of the blood were removed and mixed with 6 mL of the novel nucleic acid preservation solution (15 mM GSH, 2M LiCl, 0.7 M GnHCl, 8 M urea, 100 mM Spermidine, 30 mM Biuret and 5 mM EDTA) and stored at room temperature for 12 days. At time 0, 6 days and 12 days, RNA was isolated from the preserved blood using Norgen Biotek Blood RNA/DNA Preservation and Isolation Kit (Cat #48900, Norgen Biotek Corp., Thorold, Canada) in triplicate from 3 different donors. Briefly, 1.5 mL RNA Extraction Buffer A and 1.5 mL RNA Extraction Buffer were added to the 9 mL preserved blood sample and vortexed for 30 seconds at high speed. Next, the tube was incubated at −20° C. for 10 minutes, followed by centrifugation at 6,000 RPM for 25 minutes. The supernatant was decanted and 570 μL of Resuspension Buffer was added to the pellet and the tube was vortexed. Next, 330 μL of 95% ethanol was added to the tube and the tube again vortexed to mix. Next, 450 μL of the lysate was added to a silicon carbide-based spin column and centrifuged for 1 minute at 14,000 rpm. This binding step was repeated with the remaining 450 μL of lysate. The column was then washed 3 times with 600 μL of Wash Solution by spinning at 14,000 rpm for 1 minute. A dry spin was then performed by spinning at 14,000 rpm for 3 minutes. The RNA was eluted in 100 μL of Elution Buffer by spinning at 2,000 rpm for 2 minutes followed by 14,000 rpm for 2 minutes. To analyze the integrity of the RNA 10 μL of each 100 μL elution was loaded onto a 1×MOPS 1.0%-Formaldehyde-agarose gel.

Figure 10:
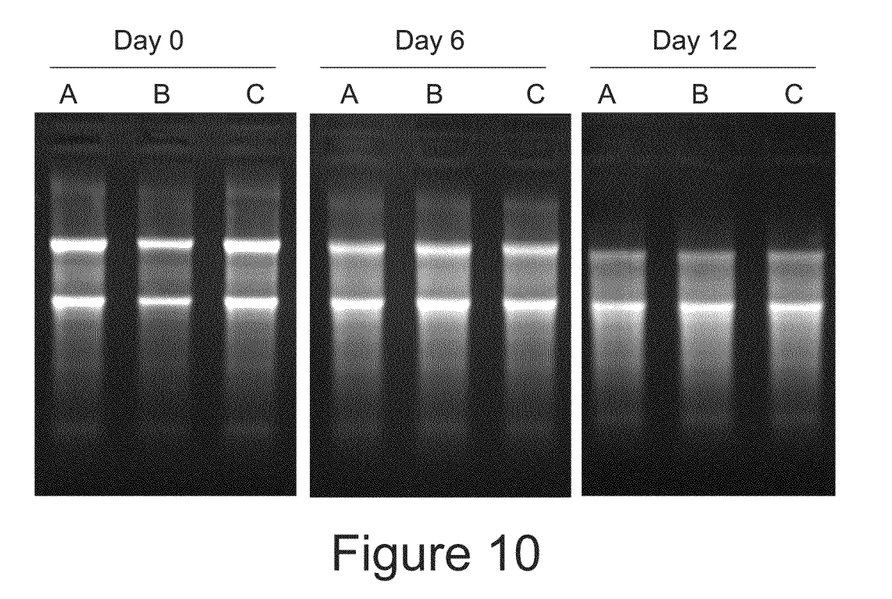
FIG. 10 shows formaldehyde-agarose gel images showing preservation and stabilization of blood RNA from 3 different donors (A, B and C) after storage for 12 days at room temperature. The blood RNA was isolated from blood treated with a nucleic acid preservative as disclosed herein.

The gel images in FIG. 10 clearly indicate that blood RNA which had been stored in the preservation solution for up to 12 days at room temperature had been preserved and stabilized (i.e. non-degraded), as both the 28S rRNA and 18S rRNA show as a clear band that is still intact from all 3 donors.

Example 3

Stability of mRNA Levels in Human Blood Preserved in Novel Nucleic Acid Preservative The preservation and stabilization over time of certain mRNA species present in blood preserved in the novel nucleic acid preservative was examined in order to determine if the preservative was indeed blocking gene induction and maintaining the expression profile of the RNA species over time. The mRNA species which were investigated included the mRNA of the housekeeping gene 18s rRNA, as well as the transcripts for the Fos-gene and IL 1B-gene.

Fifty mL blood samples were obtained from three individual donors by drawing 10 mL blood samples into BD Vacutainer™ Tubes supplemented with sodium heparin. Immediately 3 mL aliquots of the blood were removed and mixed with 6 mL of the novel nucleic acid preservation solution (15 mM GSH, 2M LiCl, 0.7 M GnHCl, 8 M urea, 100 mM Spermidine, 30 mM Biuret and 5 mM EDTA) and stored at room temperature for 12 days. At time 0, days and 12 days RNA was isolated from the preserved blood using Norgen Biotek Blood RNA/DNA Preservation and Isolation Kit (Cat #48900, Norgen Biotek Corp., Thorold, Canada) from the 3 different donors. Briefly, 1.5 mL RNA Extraction Buffer A and 1.5 mL RNA Extraction Buffer was added to the 9 mL preserved blood sample and vortexed for 30 seconds at high speed. Next, the tube was incubated at −20° C. for 10 minutes, followed by centrifugation at 6,000 RPM for 25 minutes. The supernatant was decanted and 570 µL of Resuspension Buffer was added to the pellet and the tube was vortexed. Next, 330 µL of 95% ethanol was added to the tube and the tube again vortexed to mix. Next, 450 µl of the lysate was added to a silicon carbide-based spin column and centrifuged for 1 minute at 14,000 rpm. This binding step was repeated with the remaining 450 µL of lysate. The column was then washed 3 times with 600 µL of Wash Solution by spinning at 14,000 rpm for 1 minute. A dry spin was then performed by spinning at 14,000 rpm for 3 minutes. The RNA was eluted in 100 µL of Elution Buffer by spinning at 2,000 rpm for 2 minutes followed by 14,000 rpm for 2 minutes.

After blood RNA isolation, the RNA was analyzed by RT-qPCR amplification using the 3 different primers for the 3 different mRNA species. The conditions of the reverse transcription were:

RT Mix:
4 µL of RNA
1 µL of Gene reverse primer (100 µM)
4 µL 5× First Strand Buffer (SuperScript™ III Reverse Transcriptase (Invitrogen, Cat. No. 18080-093)
2 µL DTT
1 µL 10 mM dNTPs
0.5 µL SSIII
7.5 µL Water
(SuperScript™ III Reverse Transcriptase, Invitrogen, Cat. No. 18080-093)
RT Program:

| Cycle 1: (1X) | |
|---|---|
| Step 1: | 65.0° C. for 05:00 minutes |
| Cycle 2: (1X) | |
| Step 1: | 25.0° C. for 05:00 minutes |
| Step 2: | 50.0° C. for 25:00 minutes |
| Cycle 3: (1X) | |
| Step 1: | 70.0° C. for 10:00 minutes |
| Cycle 4: (1X) | |
| Step 1: | 4.0° C. for 99:99 minutes | qPCR Mix
5 µL cDNA
10 µL 2×SYBR Green Mix
0.12 µL Gene Forward Primer (100 µM)
0.12 µL Gene Reverse Primer (100 µM)
4.76 µL water
qPCR Program

| Cycle 1: (1X) | |
|---|---|
| Step 1: | 95.0° C. for 03:00 minutes |
| Cycle 2: (40X) | |
| Step 1: | 95.0° C. for 00:15 seconds |
| Step 2: | 60.0° C. for 00:30 seconds |
| Step 3: | 72.0° C. for 00:45 seconds |
| Data collection and real-time analysis enabled. | |
| Cycle 3: (1X) | |
| Step 1: | 57.0° C. for 01:00 minute |
| Cycle 4: (80X) | |
| Step 1: | 57.0° C. for 00:10 seconds |
| Increase setpoint temperature after cycle 2 by 0.5° C. | |
| Melt curve data collection and analysis enabled. | |

Figure 11:
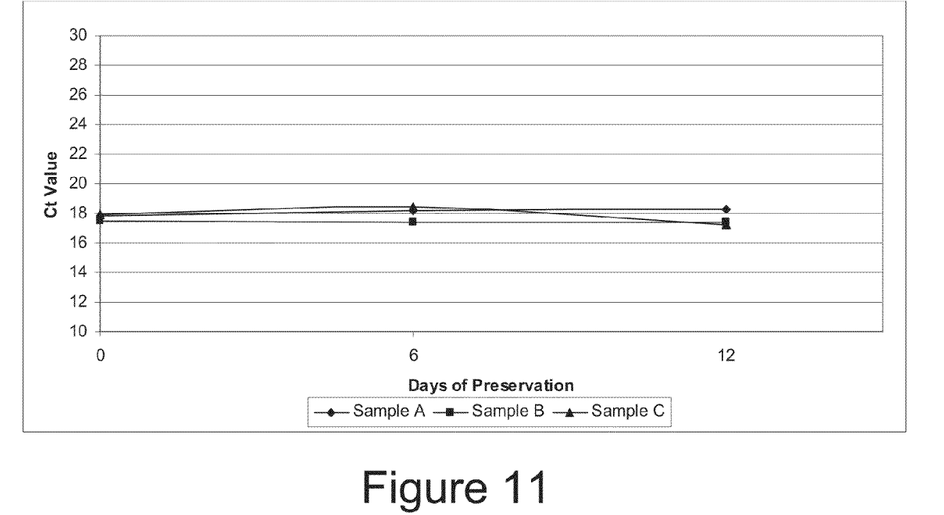
FIG. 11 is a line graph showing the Ct value for the 18S rRNA gene isolated from the blood of 3 different donors (A, B and C) after storage for 0 days, 6 days and 12 days at room temperature. The RNA was isolated from blood treated with a nucleic acid preservative as disclosed herein.
Figure 12:
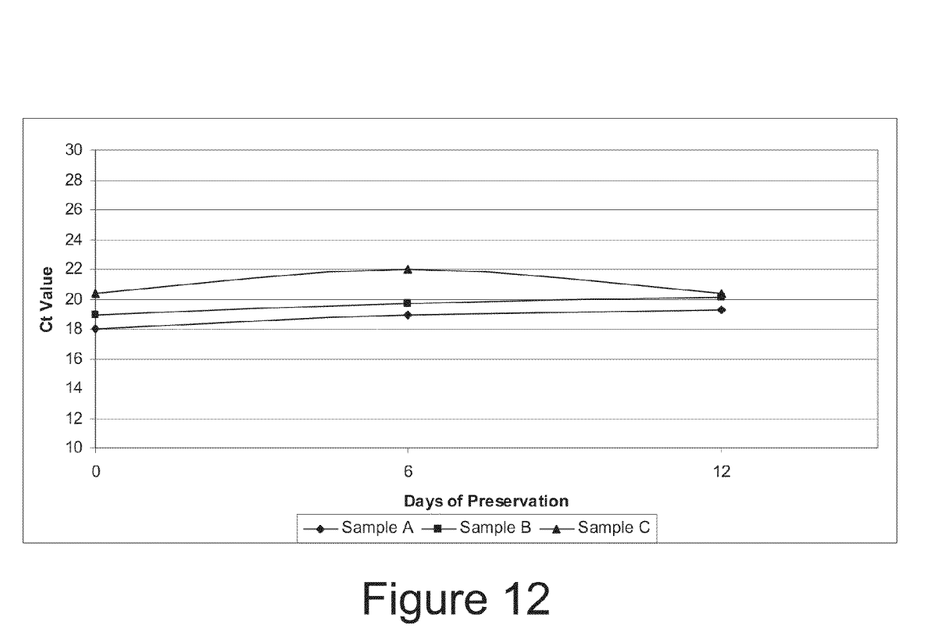
FIG. 12 is a line graph showing the Ct value for the FOS gene mRNA isolated from the blood of 3 different donors (A, B and C) after storage for 0 days, 6 days and 12 days at room temperature. The RNA was isolated from blood treated with a nucleic acid preservative as disclosed herein.
Figure 13:
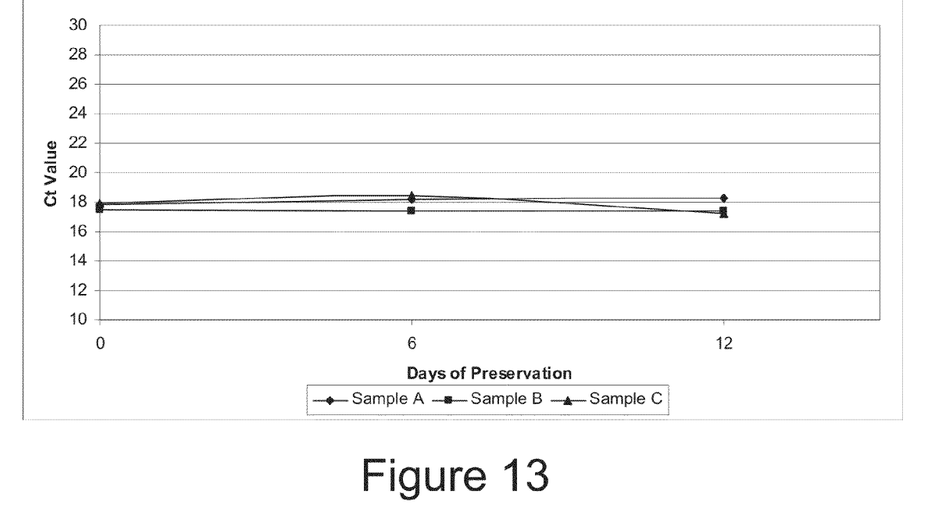
FIG. 13 is a line graph showing the Ct value for the IL1B-gene mRNA isolated from the blood of 3 different donors (A, B and C) after storage for 0 days, 6 days and 12 days at room temperature. The RNA was isolated from blood treated with a nucleic acid preservative as disclosed herein.

The Ct (cycle threshold) values generated from the qPCR for each donor were then graphed from day 0 to day 12 for the 18s rRNA gene (FIG. 11), the Fos-gene (FIG. 12) and IL1B-gene (FIG. 13). From FIG. 11-13, it can be seen that the Ct values changed only minimally over time, indicating indeed that the mRNA was preserved and stable, and that there were not changes in gene expression indicating that gene induction was prohibited.

Example 4

Stability of microRNA Levels in Human Plasma Preserved in Novel Nucleic Acid Preservative The preservation and stabilization over time of certain microRNA (miRNA) species present in plasma in the novel nucleic acid preservative was examined in order to determine if the preservative was indeed blocking gene induction and maintaining the expression profile of the miRNA species over time. The miRNA species which were investigated included let-7a, miR-93, miR-103, miR-451, miR423-5p, miR-192 and miR-16.

Fifty mL blood samples were obtained from one donor by drawing 10 mL blood samples into BD Vacutainer™ Tubes supplemented with sodium heparin. Plasma was processed immediately from the collected blood by centrifugation in a standard swing-bucket centrifuge at 2,000 RPM for 15 minutes. Using a disposable transfer pipette, the upper plasma fraction was collected. Immediately 3 mL aliquots from the processed plasma were removed and mixed with 6 mL of a nucleic acid preservation solution (15 mM GSH, 2M LiCl, 0.7 M GnHCl, 8 M urea, 100 mM Spermidine, 30 mM Biuret and 5 mM EDTA) and stored at room temperature for 12 days. At time 0, 6 days and 12 days plasma RNA was isolated from the preserved plasma using Norgen Biotek Blood RNA/DNA Preservation and Isolation Kit (Cat #48900, Norgen Biotek Corp., Thorold, Canada). Briefly, 1.5 mL RNA Extraction Buffer A and 1.5 mL RNA Extraction Buffer were added to the 9 mL preserved plasma sample and vortexed for 30 seconds at high speed. Next, the tube was incubated at −20° C. for 10 minutes, followed by centrifugation at 6,000 RPM for 25 minutes. The supernatant was decanted and 570 µL of Resuspension Buffer were added to the pellet and the tube is vortexed. Next, 330 µL of 95% ethanol was added to the tube and the tube again vortexed to mix. Next, 450 µL of the lysate was added to a silicon carbide-based spin column and centrifuged for 1 minute at 14,000 rpm. This binding step was repeated with the remaining 450 µL of lysate. The column was then washed 3 times with 600 µL of Wash Solution by spinning at 14,000 rpm for 1 minute. A dry spin was then performed by spinning at 14,000 rpm for 3 minutes. The RNA was eluted in 100 µL of Elution Buffer by spinning at 2,000 rpm for 2 minutes followed by 14,000 rpm for 2 minutes.

After plasma RNA isolation, the plasma miRNA was analyzed by RT-qPCR amplification using the different primers for the 7 different miRNA species and the miRCURY LNA Universal RT miRNA PCR Kit. The conditions of the reverse transcription are:
RT Mix:
4 mL of RNA used in a 20 mL RT reaction using miRCURY LNA Universal RT miRNA PCR
RT Program:

| Cycle 1: (1X) | |
|---|---|
| Step 1: | 65.0° C. for 05:00 minutes |
| Cycle 2: (1X) | |
| Step 1: | 25.0° C. for 05:00 minutes |
| Step 2: | 50.0° C. for 25:00 minutes |
| Cycle 3: (1X) | |
| Step 1: | 70.0° C. for 10:00 minutes |
| Cycle 4: (1X) | |
| Step 1: | 4.0° C. for 99:99 minutes | qPCR Mix
5 µL cDNA
10 µL 2×SYBR Green Mix
0.12 µL Gene Forward Primer (100 µM)
0.12 µL Gene Reverse Primer (100 µM)
4.76 µL water
qPCR Program

| Cycle 1: (1X) | |
|---|---|
| Step 1: | 95.0° C. for 03:00 minutes |
| Cycle 2: (40X) | |
| Step 1: | 95.0° C. for 00:15 seconds |
| Step 2: | 60.0° C. for 00:30 seconds |
| Step 3: | 72.0° C. for 00:45 seconds |
| Data collection and real-time analysis enabled. | |
| Cycle 3: (1X) | |
| Step 1: | 57.0° C. for 01:00 minute |
| Cycle 4: (80X) | |
| Step 1: | 57.0° C. for 00:10 seconds |
| Increase setpoint temperature after cycle 2 by 0.5° C. | |
| Melt curve data collection and analysis enabled. | |

Figure 14:
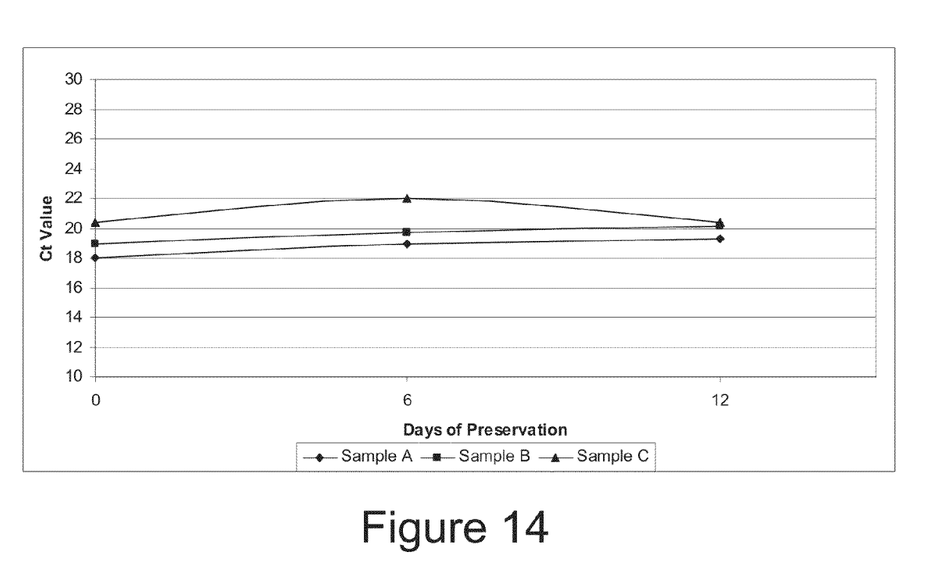
FIG. 14 is a line graph showing the Ct value for 7 different microRNA species isolated from plasma after storage for 0 days, 6 days and 12 days at room temperature. The RNA was isolated from plasma treated with a nucleic acid preservative as disclosed herein.

The Ct values generated from the RT-qPCR were then graphed from day 0, day 6 and day 12 for the 7 different miRNA genes (FIG. 14). From FIG. 14, it can be seen that the Ct values changed only minimally over time, indicating that indeed the miRNA was stable and preserved, and that there were no changes in gene expression indicating that gene induction was prohibited.

The invention claimed is:
1. A composition for preserving nucleic acids comprising:
   a reducing agent, glutathione, wherein the glutathione is present in an amount from about 10 mM to about 200 mM;
   a first chaotropic substance, LiCl, wherein the LiCl is present in an amount of from about 1 M to about 4 M;
   a second chaotropic substance, guanidine hydrochloride, wherein the guanidine hydrochloride is present in an amount from about 0.1 M to about 0.9 M;
   a third chaotropic substance, urea, wherein the urea is present in an amount from about 2 M to about 12 M;
   a first polyamine substance, spermidine, wherein the spermidine is present in an amount from about 10 µM to about 300 µM;
   a second polyamine substance, biuret, wherein the biuret is present in an amount of from about 10 mM to about 100 mM;
   and a chelating agent, EDTA, wherein the EDTA is present in an amount of from about 1 mM to about 200 mM.
2. The composition according to claim 1, further comprising a biological sample.
3. The composition according to claim 2, wherein said biological sample is blood and the ratio of the composition to blood is 3:1 to about 1:1 v/v.
4. The composition according to claim 2, wherein said biological sample is blood and the ratio of the composition to blood is 2:1 v/v.

* * * * *